United States Patent [19]
Michelson

[11] Patent Number: 5,662,300
[45] Date of Patent: Sep. 2, 1997

[54] GOOSENECK SURGICAL INSTRUMENT HOLDER

[76] Inventor: Gary Karlin Michelson, 438 Sherman Canal, Venice, Calif. 90291

[21] Appl. No.: 552,203

[22] Filed: Feb. 7, 1996

Related U.S. Application Data

[62] Division of Ser. No. 97,945, Jul. 26, 1993, Pat. No. 5,513,827.

[51] Int. Cl.$^6$ ............................................. A61B 19/00
[52] U.S. Cl. .................. 248/279.1; 248/160; 248/183.1; 248/286.1
[58] Field of Search ......................... 248/279.1, 285.1, 248/286.1, 160, 183.1, 225.11; 128/20

[56] References Cited

U.S. PATENT DOCUMENTS

| | | | |
|---|---|---|---|
| 870,429 | 11/1907 | Grimler | 248/160 |
| 1,279,803 | 9/1918 | Watson | 248/160 |
| 3,133,719 | 5/1964 | Beck | 248/316.1 X |
| 3,329,149 | 7/1967 | Kendall et al. | 248/278 X |
| 3,858,578 | 1/1975 | Milo | 128/20 |
| 4,457,300 | 7/1984 | Budde | 128/20 |
| 4,573,452 | 3/1986 | Greenberg | 128/20 |
| 4,617,916 | 10/1986 | LeVahn et al. | 128/20 |
| 4,863,133 | 9/1989 | Bonnell | 248/278 |
| 4,867,404 | 9/1989 | Harrington et al. | 248/276 X |
| 5,279,281 | 1/1994 | Harvey | 128/4 |
| 5,284,130 | 2/1994 | Ratliff | 248/160 X |
| 5,348,259 | 9/1994 | Blanco et al. | 248/276 |

FOREIGN PATENT DOCUMENTS 1489731  6/1989  U.S.S.R. .................. 128/20

OTHER PUBLICATIONS

"Micro Retractors, Brain", Codman, (No Date) pp. 343–344.

Primary Examiner—Ramon O. Ramirez
Attorney, Agent, or Firm—Lewis Anten, Esq.; Amedeo Ferraro, Esq.

[57] ABSTRACT

A gooseneck instrument holder having an instrument holder tip, a gooseneck, a base and a detachable fibre optic light cord is disclosed. The tip, gooseneck, and base are connected by means of a cable which passes through a deflection member in the base. Tension on the cable is adjusted by a detachable handle at the base via a bolt and serves to simultaneously tighten the tip about an instrument, to hold the gooseneck in place, and to hold the base steady so that the holder holds an instrument in place. Very small amounts of turning of the handle is necessary to adequately tighten the holder in place.

20 Claims, 9 Drawing Sheets

GOOSENECK SURGICAL INSTRUMENT HOLDER

This application is a division of application Ser. No. 08/097,945, filed on Jul. 26, 1993; now U.S. Pat. No. 5,513,827.

BACKGROUND

1. Field of the Invention

This invention relates to surgical equipment used in surgery and more particularly to surgical instrument positioning and holding means for aiding surgeons by acting as an extra hand.

2. Description of the Related Art

Prior instrument holders have been bulky and unwieldy, protruding across the operating area in order to provide great adjustability and access to the entire operating area for the instrument held. When put into use, the surgeon would sometimes have to work around the instrument holder when the instrument holder is actually there to accommodate the surgeon. While enabling some enhancements to surgical procedures, prior instrument holders did not perform as well as might be expected.

A variety of devices have been developed to assist at surgery for the purpose of three dimensionally positioning and then holding a surgical instrument. One variety of such devices utilizes a series of bars and clamps, with a terminal clamp positioned to assist in the instrument being held.

An improvement on such a device is a flexible arm device made up of a series of interlockable segments strung on a cable such that all of the segments have some freedom of movement along this cable, but when the cable is tightened the segments are pulled together and the individual segments become fixed. This is known as a gooseneck holder. While the ability to move one variable arm is an advantage over the need to simultaneously control multiple connections, as in the rod and clamp type devices, some significant problems still persist.

First, since it is necessary for the gooseneck holder arm to both reach the full extent of where it needs to go and yet be able to work close to its point of origin, it must be twice as long as the needed reach to be capable of being doubled back to return its point of origin. This is a problem because as the length of the arm and the number of segments is increased the device becomes less rigid, less stable and requires more and more cable excursion and force to gain any significant segment to segment interlock.

Secondly, while the flexible arm portion itself is stabilized by a fixed windlass mechanism at the base, this does not control the terminal instrument grasping clamp so that the surgeon must still contend with controlling several things at once.

Thirdly, while working with the holder in any position other than fully extended, the redundant portion is often a hindrance to the surgeon, compromising his visualization or access into the wound or obstructing the path of his hand as he works.

Fourthly, because of the relative long length of the flexible segments made necessary by its need to retain the capacity of being workable close to its origin, as well as at its furthest reach, the windlass mechanism needs to be of considerable length and have a relatively large handle to be able to tighten up sufficient cable slack and to have sufficient mechanical advantage so as to generate the force needed to actively pull the segments tight enough to effect a relative lock. The bulk of the positioning windlass and handle obstruct the surgeon's access and the movement of his hands about the wound, and compromises the passing of instruments into and out of the wound.

Fifthly, the long flexible arm and cable length have required multiple turns of the handle to tighten the segments of the gooseneck. Such turning is generally a problem because of the proximity of the base to the patient's body making such movements difficult.

Sixthly, the terminal instrument grasping clamp has generally been a grasp clamp bound centrally to the flexible arm and with a handle extending from one end and the grasping means or clamp portion from the other end. This is constantly in the surgeon's way, interfering with his line of sight and the free movement of his hand.

There is therefore a need for a clamp device embodying the advantages of a flexible gooseneck arm but improving it so that it is less intrusive, more efficient, and more adjustably deployable. There is also a need to eliminate the need for redundancy in the length of the flexible arm and a need for a simple means to lock the flexible segments, the terminal instrument grasping portions, and the support base in place.

SUMMARY OF THE INVENTION

The gooseneck instrument holder of the present invention has a slider support base that contains the means to lock all of the adjustable features of the holder. The slider support base slides in the slot of a bar and is connected to a gooseneck consisting of a series of individual segments strung on a central cable. One end of the cable is connected to a bolt. The other end of the cable is connected to an instrument holder tip which has a hole or opening through which the shaft of an instrument may be inserted. The operation of the instrument holder is controlled by the cable that runs the length of the gooseneck. When the bolt in the support base attached to one end of the cable is turned, the attached cable pulls at the instrument holder tip so that the shaft of an instrument held in the opening is trapped between the opening wall and the top segment of the gooseneck. The turning of the bolt also increases the friction between the articulating gooseneck segments so that they remain in place. The cable passes through a deflection member in the form of a hole in a freely sliding member that passes through the slot in the base plate. The slider support base itself is also held in place when the cable is made taut by pulling up on the deflection member. Therefore, by just tightening the cable, the gooseneck instrument holder is ready to perform in the surgical area by holding in place the instrument, and the gooseneck holder acts as an extra hand for the surgeon.

OBJECTS OF THE INVENTION

It is an object of the present invention to physically and visually unclutter the surgical area by holding instruments in an unobtrusive way.

It is a further object of the present invention to provide a gooseneck instrument holder that has a multitude of independently adjustable segments allowing redundantly for universal motion and such that all segments may be locked firmly with a single motion with a single control.

It is yet a further object of the present invention to provide a gooseneck instrument holder that is easily adjusted and set into position.

It is another object of the present invention to provide an instrument holder that cannot crush the held instrument.

It is a yet another object of the present invention to provide an instrument holder that can be set into position with a single control.

It is still another object of this invention to provide an instrument holder that may have its internal tension distribution adjustably altered.

It is yet a further object of the present invention to provide an instrument holder with a windlass winding device which may be identical to the windlass device already used for the underlying retractor.

It is also another object of the present invention to provide an instrument holder that is workable from either side of a retractor.

It is another object of the present invention to provide an instrument holder that is easy to place or remove but which remains firmly based when in use.

These and other objects of the present invention will be evident from a review of the following specification and the accompanying drawings.

DETAILED DESCRIPTION OF THE PREFERRED EMBODIMENTS

FIGS. 1–6B show the preferred embodiment of the present invention of an instrument holding assembly having a flexible gooseneck. The gooseneck instrument holder is referred to generally by reference number 200.

The gooseneck instrument holder 200 has a generally rectangular retractor baseplate 202 with a central longitudinal slot 204 extending substantially the length of the retractor baseplate 202. Extending downward from opposite ends of the bottom surface of the retractor baseplate 202 are two downwardly chamfered or slightly tapered, cylindrical support posts 206 and 208. The support posts 206 and 208 fit within generally elliptical holes 210 and 212 present in the arm of a crank frame retractor A' such as disclosed in U.S. Pat. No. 5,052,373, issued Oct. 1, 1991. The elliptical holes 210 and 212 may be straight walled or may also be cone or funnel shaped so that the slightly tapered cylindrical support posts 206 and 208 can easily fit in and out of the elliptical holes 210 and 212 if lifted straight up and out with no other forces applied, but if cantilevered or holding something, the support posts 206 and 208 may not be easily removed from the elliptical holes 210 and 212. The elliptical holes 210 and 212 permit the support posts 206 and 208 to be more easily inserted into the crank frame arm A' while providing a snug and secure fit. Alternatively, as it is often easier to fit one of the support posts 206 or 208 into the retractor arm A', only one of the holes 210 and 212 may be elliptical so that the second support post 206 or 208 may be more easily attached to the frame arm A'. While the present invention is described in association with the use of the arm of a crank frame retractor, it may be mounted on any number of other instruments, supports, or frames.

Figure 1:
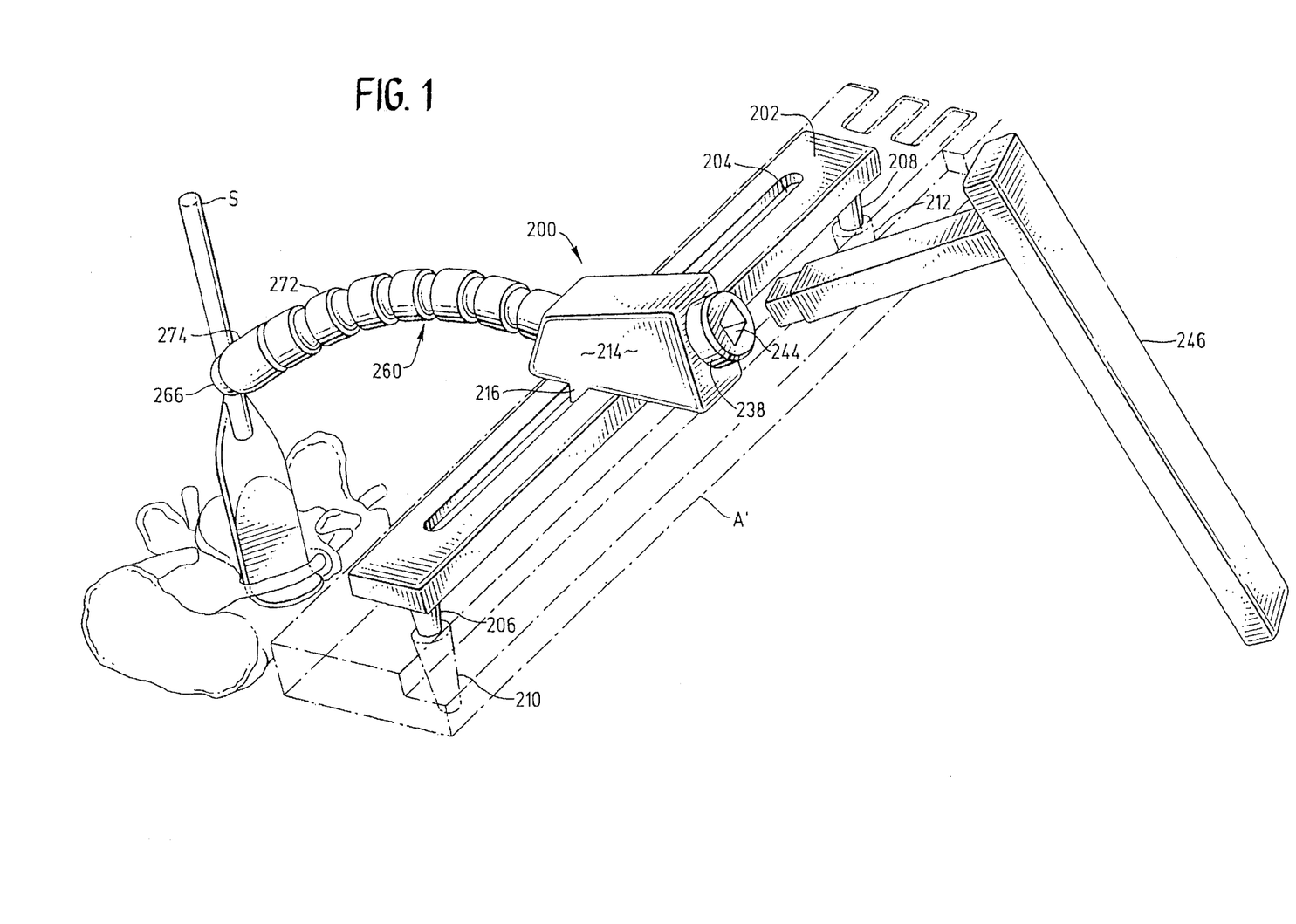
FIG. 1 is a perspective view of the gooseneck instrument holder.
Figure 2:
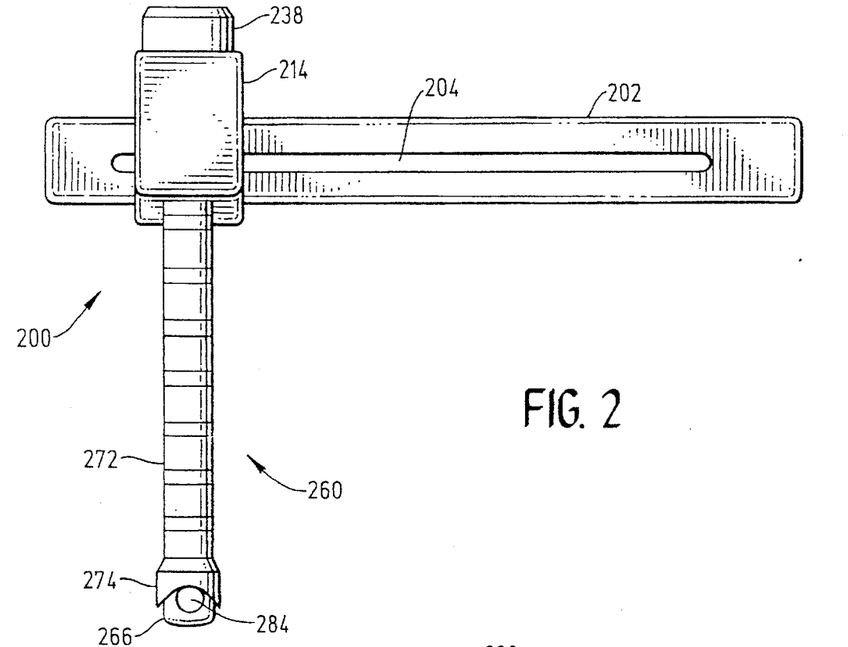
FIG. 2 is a top view of the gooseneck instrument holder.
Figure 3:
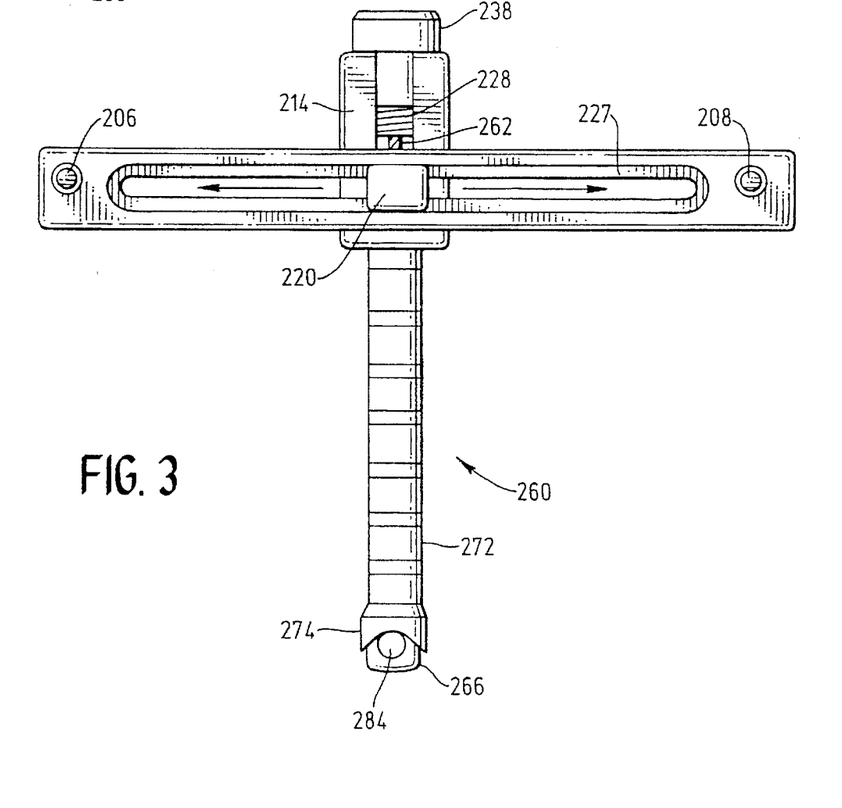
FIG. 3 is a bottom view of the gooseneck instrument holder.
Figure 4:
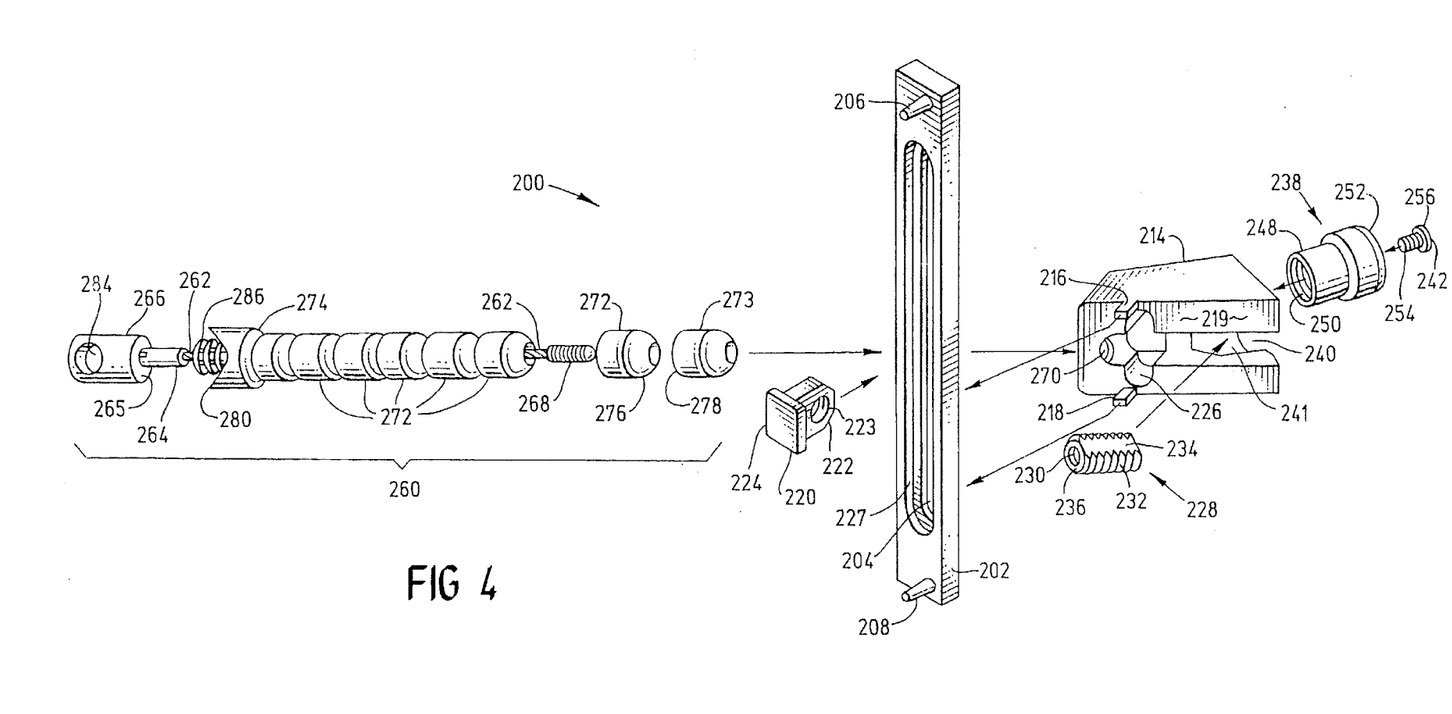
FIG. 4 is an exploded, perspective, bottom view of the gooseneck instrument holder.
Figure 5:
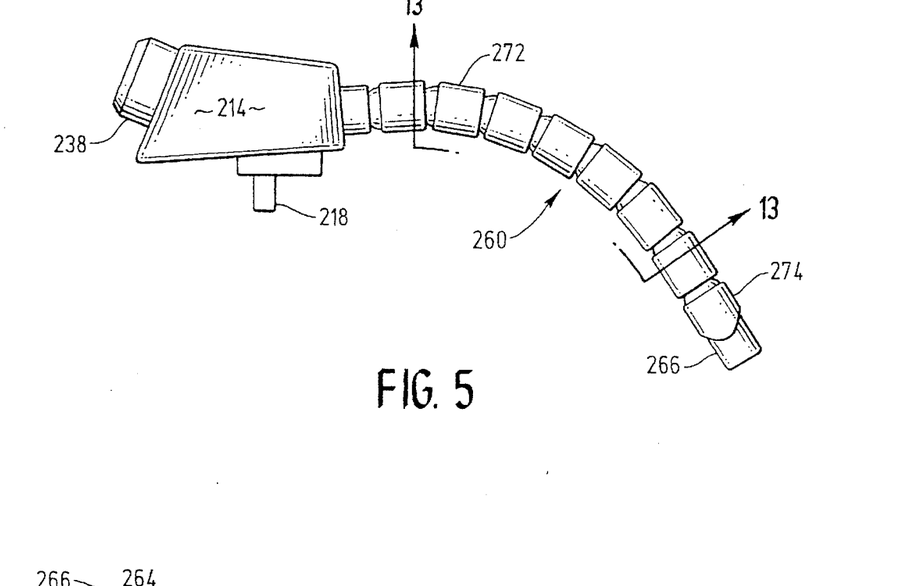
FIG. 5 is a side view of the gooseneck instrument holder without the base and having a fibre optic light cord disposed within the gooseneck portion.

As shown more clearly in FIG. 4, a slider block 214 has two short arms 216 and 218 extending downwardly from the bottom surface 219 of the slider block 214. The short arms 216 and 218 correspond in width to the width of the central slot 204 in retractor baseplate 202 so that the slider block 214 can slide in the central slot 204.

Slider block 214 is slidably attached to retractor baseplate 202 by means of slider pin 220 which has an upper key portion 222 having a width slightly smaller than the width of central slot 204, an opening 223 on the upper key portion 222 having the cross section surface of the opening 223 in the plane of the axis of the central slot 204. The slider pin 220 has a lower base portion 224 having a width wider than the central slot 204. The upper key portion 222 of slider pin 220 extends through the central slot 204 and into a key hollow 226 present between the two short arms 216 and 218 of the slider block 214. The purpose of the opening 223 in slider pin 220 will be disclosed below.

The lower base portion 224 of slider pin 220 prevents the upper key portion 222 from passing through the central slot 204. The slider pin lower base portion 224 is flat and fits within a recess 227 present in the bottom of retractor baseplate 202. The recess 227 is wider than the central slot 204 and allows the slider pin lower base portion 224 to fit flush with the bottom of the retractor baseplate 202 without allowing the slider pin 220 to pass completely through the retractor baseplate central slot 204. As will be seen below, the slider pin 220 is coupled to the slider block 214 by a cable 262 passing through the slider block 214 and the opening 223 so that the slider block 214 will not become detached from the retractor baseplate 202.

A hollow tubular threaded pin 228 also fits within a hollow 240 of the slider block 214. The threaded pin 228 is threaded both internally 230 and externally 232. In order to prevent the threaded pin 228 from turning or rotating within the slider block 214, the threaded pin 228 has two opposing flat sides 234 and 236 that correspond to hollow 240 in slider block 214 which has a flattened side wall at its lower end and is round at its upper end. The threaded pin 228 can move laterally along its length, sliding within the confines of the hollow 240 in slider block 214.

At the entrance to hollow 240 in the slider block 214, a bolt 238 fits within the upper end of hollow 240 within the slider block 214. The bolt 238 is hollow and has a reduced diameter portion 248 so that the threaded pin 228 can fit within the bottom interior of bolt 238. A screw 242 fits within the upper end of bolt 238, and screws into the interior of threaded pin 228. The bolt 238 has a square head depression 244 so that a square head wrench 246 can turn the bolt 238 within the slider block 214. The square head wrench 246 may be the same wrench used to adjust the underlying crank frame retractor A' or other instruments or supports to which the gooseneck instrument holder 200 is attached so that the square head wrench 246 is interchangeable.

The bolt 238 is internally threaded at its reduced diameter portion 248. These internal bolt threads 250 correspond to and engage the exterior threads 232 of the upper portion of threaded pin 228. When the bolt 238 is turned by the square head wrench 246, the flat sides 234 and 236 of the threaded pin 228 are fitted within the flat sides of hollow 240 to prevent threaded pin 228 from turning within the lower portion of slider block 214. Since the bolt 238 is able to turn within the cylindrical upper portion 241 of the slider block 214 while the threaded pin 228 is not, the turning of bolt 238 draws the threaded pin 228 into or expels the threaded pin 228 out from the reduced diameter end 248 of the bolt 238.

Screw 242 fits within the rear end 252 of the bolt 238 within the center of the square head depression 244. The threaded portion 254 of the screw 242 passes through the interior of the bolt 238 so that it may engage interior threads 230 of threaded pin 228. The opening through which the screw 242 passes within the bolt 238 is narrower than the head 256 of the screw 242 so that the screw 242 cannot pass through the bolt 238.

The screw 242 serves to hold the threaded pin 228 within the bolt 238 while still allowing the threaded pin 228 to move in and out of the bolt 238. The slight motion of the threaded pin 228 made by the bolt 238 is sufficient for the purposes of this invention to provide ample utility in controlling the gooseneck instrument holder 200.

Having set forth the structure of the slider block 214 and its accompanying components, the gooseneck portion 260 of the gooseneck instrument holder is now set forth.

At the core of the gooseneck portion 260 is a cable 262. At the forward end of the cable 262 is a cable tip 264. The cable tip 264 attaches to the rear end 265 of the instrument holder tip 266 of the gooseneck portion 260. At the rear end of the cable 262 is a threaded cable tip 268. The threaded cable tip 268 passes through a cable opening 270 present at the forward end of the slider block 214, the opening 223 of the slider pin 220, and threads into the interior threads 230 of threaded pin 228. Alternatively, the threaded cable tip 268 may also be a press fitted end plug.

Surrounding the cable 262 are a series of gooseneck buttons 272. Save for the instrument holder tip button 274, each of the buttons 272 and button 273 are the same. The buttons 272 and 273 are generally cylindrical, having a spherically rounded portion convex at their rear end 276 and a spherically rounded concave portion at their forward end 278. This configuration can be reversed so that the rear end 276 is convex and the forward end 278 is concave. Alternatively the buttons 272 may be a series of balls and cups, balls and cylinders, elongated balls or any other configuration that provides the operation of a gooseneck may be used. In the present embodiment, the rounded convex rear end 276 of a button 272 fits within the rounded concave forward end 278 of the button immediately adjacent to it. Further, as the portions in contact between two adjacent buttons are spherically rounded, they are able to articulate with respect to each other. As is explained in more detail below, the buttons 272 are held together by compressive forces applied by tightening cable 262. As the buttons 272 are able to slide and articulate with respect to each other, the gooseneck portion 260 may be bent, formed or rotated into a number of convenient positions.

The cable forward facing aspect of opening 270 in slider block 214 is formed so that it matches the protruding rounded convex rear end 276 of the button 273 as if it were another adjacent button. The rear end of the instrument holder tip button 274 is the same as the rear 276 of a gooseneck button 272. However, the forward end 280 of the instrument holder tip button 274 is constructed to receive the instrument holder tip 266.

Figure 6A:
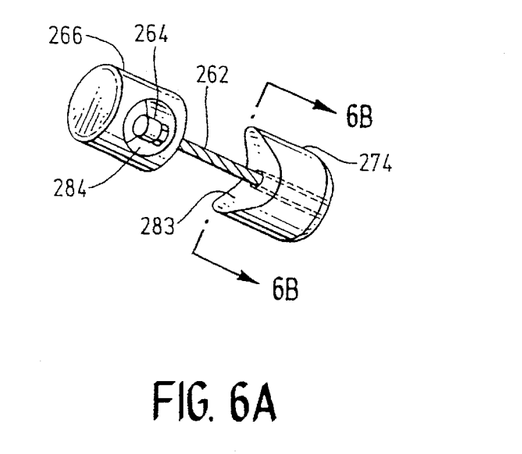
FIG. 6A is an exploded perspective view of the tip portion of the gooseneck instrument holder.
Figure 6B:
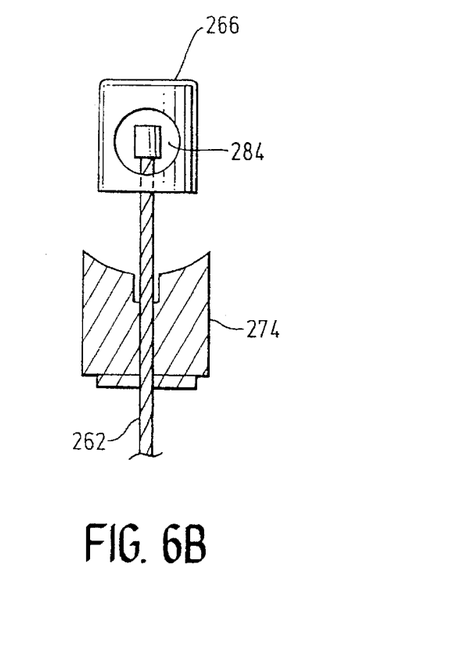
FIG. 6B is a cross section of tip portion cradling and holding the instrument holder tip.

As shown in FIGS. 6A and 6B, the instrument holder tip button 274 is v-shaped at its forward end 280 to cradle and hold firm the instrument holder tip 266. The cylindrical shaft S of an instrument may be inserted into the opening 284 of instrument holder tip 266. The instrument holder tip 266 is constructed so that the shaft S of an instrument, such as a neural retractor, fits closely within the opening 284 of the instrument holder tip 266. When the cable 262 pulls the instrument holder tip 266 towards the instrument holder tip button 274, the lower end of instrument holder tip 266 moves into the v-shaped forward end 280, pulling the shaft S of the instrument contained in tip opening 282 toward the forward end 280 of instrument holder tip button 274. This snugly holds the instrument shaft S between the instrument holder tip button 274 and the upper end of tip opening 284.

In order to allow easy insertion and removal of a shaft S from the instrument holder tip 266, a spring 286 is located between the rear end 265 of instrument holder tip 266 and instrument holder tip button 274 and urges the instrument holder tip 266 away from the instrument holder tip button 274. When there is slack in cable 262, the spring 286 urges the instrument holder tip 266 away from the instrument holder tip button 274. The tip opening 284 is then made more readily accessible for easier instrument shaft S insertion or removal. The contemplated distance of travel for the instrument holder tip 266 with respect to the instrument holder tip button 274 is only one-tenth of a millimeter. Despite this short distance, it is sufficient to securely hold shaft S while also allowing easy insertion and removal of the instrument.

The top surface 283 of the forward end 280 of instrument holder tip button 274 provides a seat for the instrument holder tip 266 so that the instrument holder tip 266 can travel only a short distance before it rests on the top surface 283 of the instrument holder tip button 274. This ensures that the gooseneck instrument holder 200 cannot be overtightened by preventing the instrument holder tip 266 and the instrument holder tip button 274 from excessively closing the tip opening 284. Therefore, the instrument shaft S held within tip opening 284 cannot be crushed between the instrument holder tip 266 and the forward end 280 of instrument holder tip button 274, yet the instrument shaft S remains firmly held in place. By stretching the desired resistance of spring 286 which may be a series of stacked spring washers such as belville washers, an instrument shaft S can be securely but adjustably held by the forces exerted by the spring 286 against the instrument holder tip 266 until the final cable tightening is completed. The spring 286 holds the instrument holder tip 266 in line with the gooseneck portion 260 while all components of the holder device remain adjustable including the rotation of the holder tip 266.

Threaded cable tip 268 of cable 262 passes through each of the gooseneck buttons 272 including the instrument holder tip button 274, into the slider block 214 through the cable opening 270, and through the slider pin opening 223. The threaded cable tip 268 of the cable 262 is then threaded into the lower end of threaded pin 228 via the interior threads 230. Since the threaded pin 228 threads into the bolt 238, turning bolt 238 increases or decreases the tension in the cable 262 (L force), and therefore the force present at the instrument holder tip 266 and instrument holder tip button 274 (T force), and the force holding the slider block 214 to the retractor baseplate 202 (S force).

The slider pin 220 serves as a means for diverting the path of the cable 262 and thus varying the relative forces associated with tightening the cable. The three forces (L, T, and S) can be relatively controlled by varying the location of the opening 223 in slider pin 220. For the gooseneck instrument holder 200, when the cable 262 is tightened by the bolt 238, the forces are distributed within the gooseneck instrument holder 200 according to the deflection of the cable by the slider pin 220 and the slider pin opening 223. The lesser deflection, the cable 262 is deflected less away from its normal course to the instrument holder tip 266. The greater the deflection, the greater force applied to the slider pin 220.

Referring to FIGS. 7–10, the height of the slider pin opening 223 can be changed to control the amount of the forces L, T, and S on the tip, line, and slider as well as the relative timing of the forces being applied. For example, if taking three different slider pins each have unique slider pin opening heights, the height being the distance from the top of the central slot 204, a position $P_1$ is furthest away from the slider pin lower base portion 224. Another slider pin opening will be between the other two in height $P_2$, and the third slider pin opening will be the lowest $P_3$ and closest to the slider pin lower base portion 224.

As the cable 262 is tightened by turning the bolt 238, more force is exerted and applied to the cable 262 (force L for line), while relatively less force is exerted by the cable 262 on the slider pin 220 as it tries to pull the slider pin 220 upwardly against the retractor baseplate central slot 204 (force S for slider). The force upon an instrument shaft S held by the instrument holder tip 266 (force T for tip) is controlled by the instrument holder tip button 274 and as set forth above, cannot exceed a certain maximum force. The force T on the tip can be different from the line force L in that the v-shaped forward end 280 provides a seat for the instrument holder tip 266 so that the instrument holder tip 266 is prevented from travelling any further than top surface 283 of the instrument holder tip button 274 as the cable is tightened by increasing the line force L. By limiting the distance that the instrument tip can travel, the force T that is applied to the instrument shaft S is also limited. In addition, when spring 286 is comprised of stacked spring washers, counterforces of the washers also act against the instrument holder tip 266. These counterforces act to hold an instrument shaft S within the instrument holder tip 266 while the other parts of the gooseneck instrument holder 200 are being adjusted.

Figure 7:
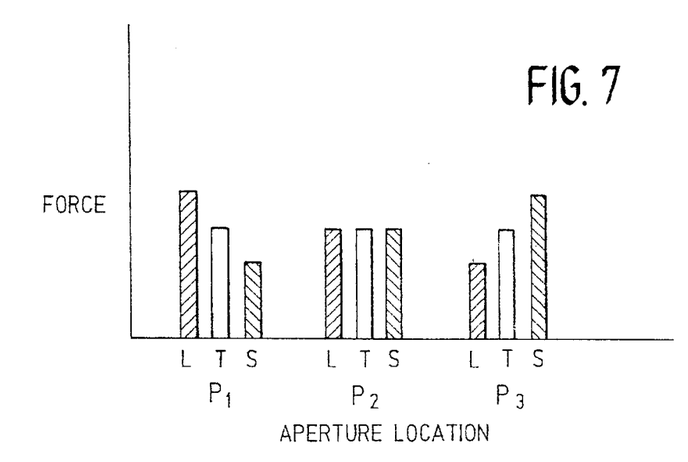
FIG. 7 is a bar graph showing relative force distributions within the gooseneck instrument holder.
Figure 8:
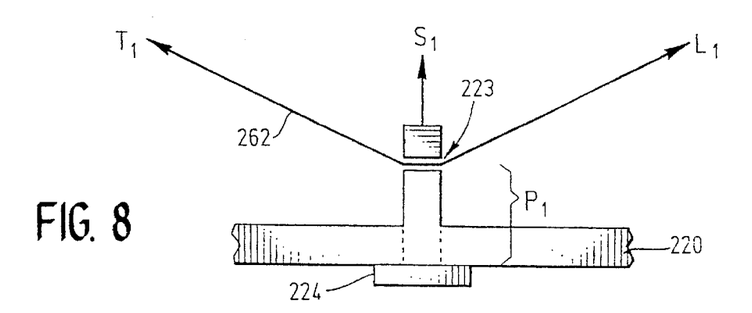
FIG. 8 is a view of the slider pin having an opening height $P_1$ showing the resulting forces $L_1$, $S_1$ and $T_1$.
Figure 9:
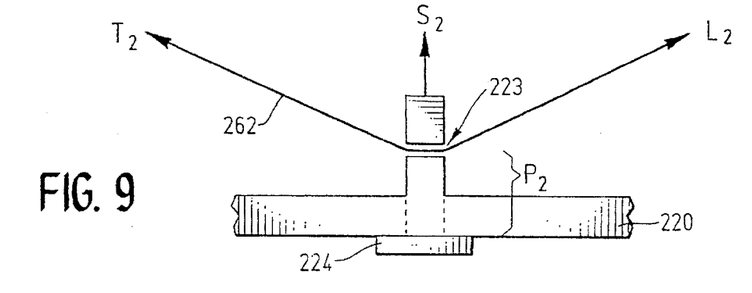
FIG. 9 is a view of the slider pin having an opening height $P_2$ showing the resulting forces $L_2$, $S_2$ and $T_2$.
Figure 10:
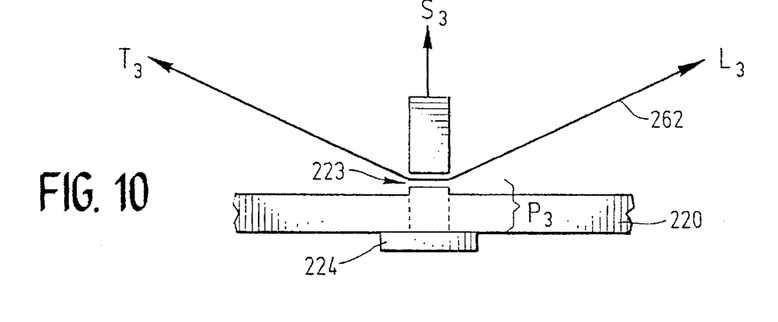
FIG. 10 is a view of the slider pin having an opening height $P_3$ showing the resulting forces $L_3$, $S_3$ and $T_3$.

For a greater cable deflection as with a $P_3$-type slider opening 223, with the opening lower, a greater force S is transmitted to the slider pin 220 and the slider block assembly 214 is more tightly held to the retractor baseplate 202 when the cable 262 is tightened by the bolt 238. For an intermediate cable deflection as with a $P_2$-type slider opening 223, forces having intermediate strengths are distributed to the line, tip, and slider. FIG. 7 shows by bar graph the relative values of exerted forces for different opening 223 locations.

When the bolt 238 is not tightened to hold an instrument shaft S at the gooseneck tip, the spring 286 applies some tension to the cable 262 and helps to keep it taut. When the cable 262 is not tightened to hold an instrument shaft S, the gooseneck portion 260 of the gooseneck instrument holder 200 can be freely flexed, bent, and twisted and the gooseneck buttons 272 articulate with respect to each other as the friction between each of the elements in the gooseneck portion 260 is relatively low. The inter-element friction may be so low as to prevent the gooseneck from holding its position once placed. If so, the bolt 238 is turned sufficiently to make taut the cable 262 so that the gooseneck portion 260 will hold a position.

When the surgeon has chosen his instrument shaft S and inserted it into the tip opening 284, the cable is made taut by turning the bolt 238. Even though the cable 262 is somewhat taut, the gooseneck portion 260 can still articulate yet hold a position once it is so placed. When the surgeon has positioned the gooseneck portion 260 in the desired position, the gooseneck instrument holder 200 is so constructed that only a one-quarter turn of the bolt 238 as applied through the square head wrench 246 is required to hold the gooseneck portion 260 in place.

Ninety to ninety-five percent of the tension needed to hold the gooseneck instrument holder 200 in place is normally kept upon the cable 262. At this tension, instruments may be inserted into the instrument holder tip 266 and the gooseneck portion 260 can be manipulated into a stable position. By turning the bolt 238 the one-quarter turn, the remaining five to ten percent of the tension required to hold an instrument shaft S in the gooseneck instrument holder 200 in place is applied. At full tension, the gooseneck instrument holder 200 stably holds the instrument shaft S in place during the surgical procedure. The one-quarter turn to fully engage the gooseneck instrument holder stands in contrast to the eight or nine turns needed for prior art instrument holders.

As only one motion, the turning of the bolt 238 by the square head wrench 246, is required to secure the instrument shaft S held at the tip to secure the position of the gooseneck portion 260, and to secure the slider block 214 to the retractor baseplate 202, an enormous advantage and convenience is provided to the surgeon as these three points of operation are simultaneously addressed and are made adjustable by the positioning of the slider pin opening 223.

A further advantage to the gooseneck instrument holder 200 is its low profile which is further enhanced by the removable square head wrench 246 which since it is removable, can be longer than customary offering the additional advantage of increased leverage. Thus, less force is required and a larger thread excursion can be utilized requiring less turns. While prior art holders were more convenient to use on the side of the patient away from the surgeon due to their high profile, the gooseneck instrument holder 200 of the present invention may be conveniently used on either side of the patient.

The gooseneck instrument holder of the preferred embodiment has the following dimensions:

The overall length of the gooseneck instrument holder 200 is approximately 6 inches. The length of the gooseneck portion 260 is approximately 4 and ¾ inches. The height of the slider block 214 is approximately 1 inch. The central slot 204 of the retractor baseplate 202 is approximately 7/32 inches wide by approximately 6 inches long. The opening 223 of the slider pin 220 has a diameter of approximately 5/32 inches. The hollow 240 of the bolt 238 has a diameter of approximately ⅝ inches. The tip opening 284 has a diameter of approximately ¼ inches. The cable 262 has an overall length of 5 and ½ inches and a diameter of 3/32 inches. The flexible shaft has a diameter of approximately 7/16 inches.

Figure 11:
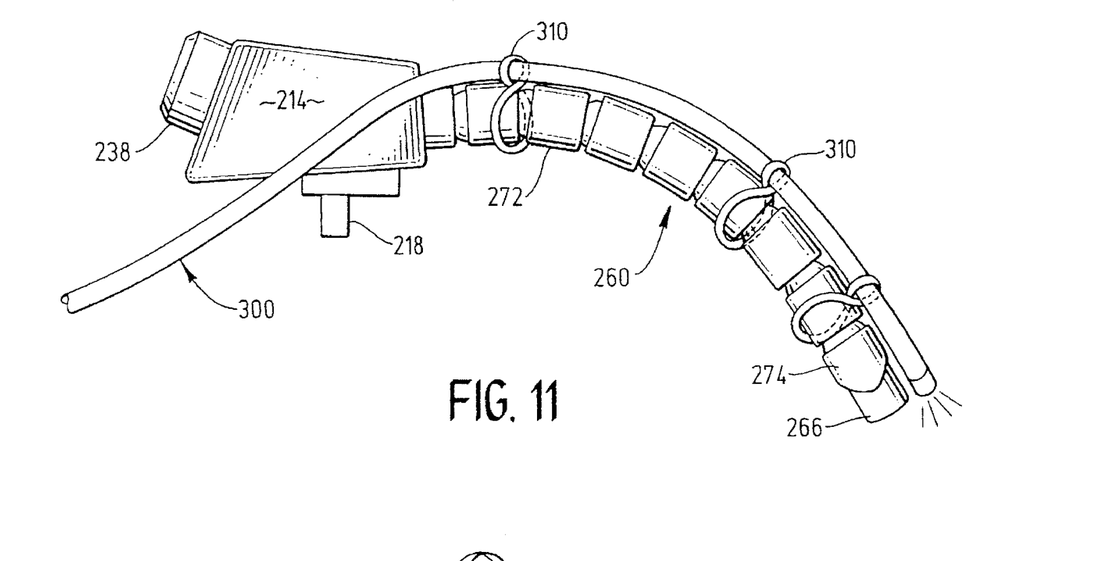
FIG. 11 is a side view of the gooseneck instrument holder without the base with a fibre optic light cord attached to the exterior of the gooseneck instrument holder.
Figure 12:
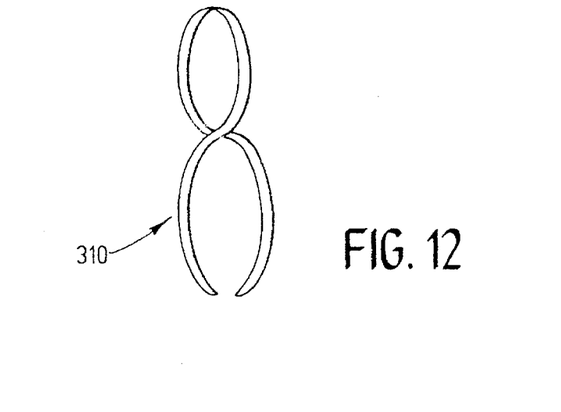
FIG. 12 is a front view of a fibre optic light cord holder used for attaching a fibre optic light cord to the exterior of the gooseneck instrument holder.
Figure 13:
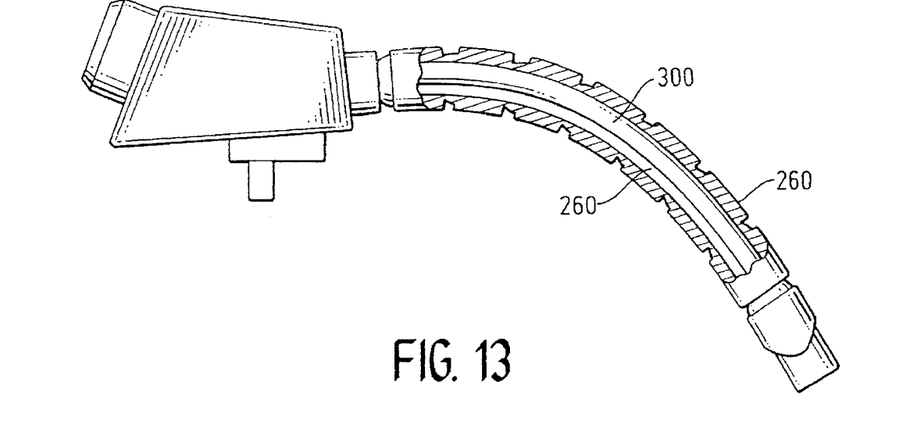
FIG. 13 is a cross section along lines 13—13 of FIG. 5 showing the cable and the fibre optic light cord within the gooseneck instrument holder.

While the present invention has been described with regards to particular embodiments, it is recognized that additional variations of the present invention may be devised without departing from the inventive concept. Referring to FIGS. 11–13, such variations include the use of fibre optics or other illumination sources associated with the instrument holder tip to illuminate the area involved in the surgical procedure.

A fibre optic light cord 300 may be attached to the gooseneck portion 260 byway of fibre optic light cord holders 310 which secure the fibre optic light cord 300 to the gooseneck buttons 272 as shown in FIGS. 11 and 12.

An alternative embodiment of the present invention is shown in FIG. 13 having a fibre optic light cord 300 contained internally within the gooseneck portion 260 so that it passes through the gooseneck buttons 272 alongside cable 262 is also within the scope of the present invention.

Further, while the gooseneck holder has been described in association with the arm of a crank frame retractor, the gooseneck holder can be used in association with any other instrument or device capable of forming a support base structure, such as a stereotactic frame or table, etc.

In an alternative embodiment, a series of openings 223a–n may be employed, with the appropriate opening selected to provide the desired characteristics of forces. Also, rather than an opening 223, slots or notches may be employed in order to direct the path of the cable.

Figure 14:
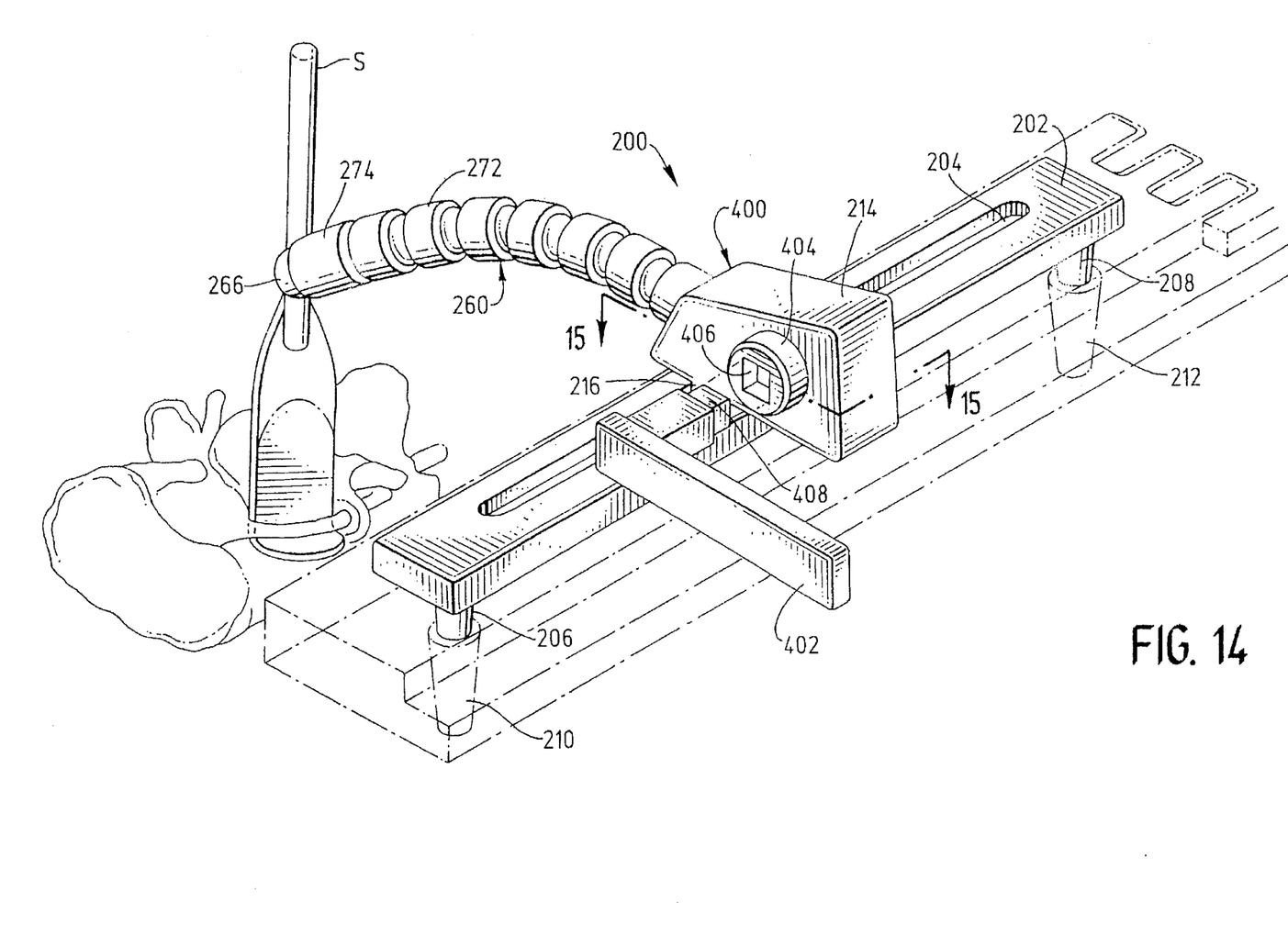
FIG. 14 is a perspective view of an alternative embodiment of the gooseneck instrument holder of the present invention having a self-locking apparatus with a removable handle for tightening the cable.
Figure 15:
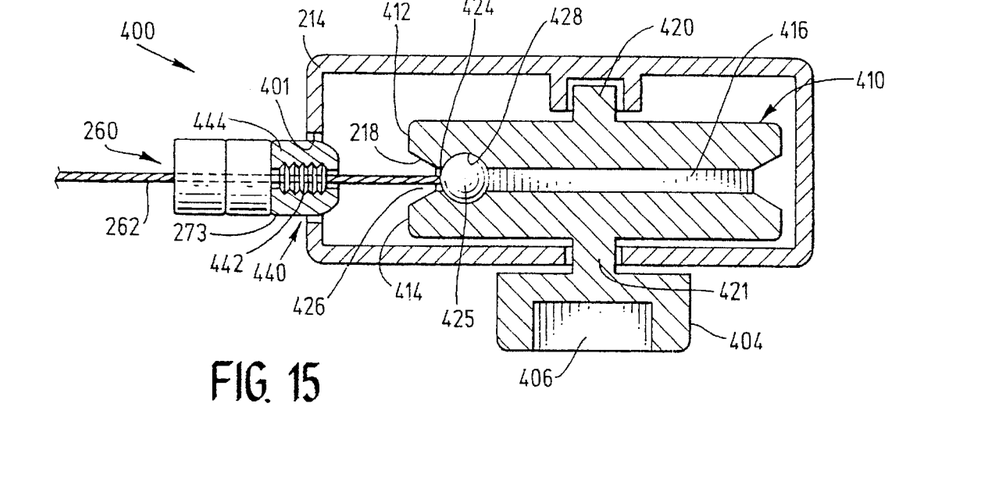
FIG. 15 is a cross-sectional view along lines 15—15 of the self-locking apparatus of the gooseneck instrument holder in FIG. 14.
Figure 16:
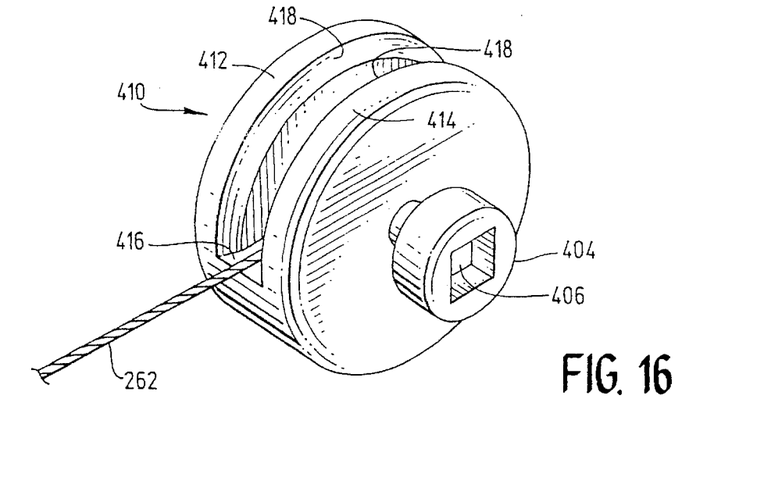
FIG. 16 is a perspective view of the central assembly of the self-locking apparatus of FIG. 15.

As shown in FIGS. 14–16, a further alternative embodiment of the gooseneck holder 200 utilizes a self-locking apparatus 400. The self-locking apparatus 400 has an off-centered, self-locking central assembly 410 that comprises two side-by-side wheels 412,414 connected to each other by a stop 416. The central assembly 410 is pivotably mounted to the slider block 214 by axles 420,421 that extend from the outer surface of the wheels 412,414 and are perpendicular to the sides of the wheels, but do not pass through the interior space between the wheels 412,414.

Figure 17:
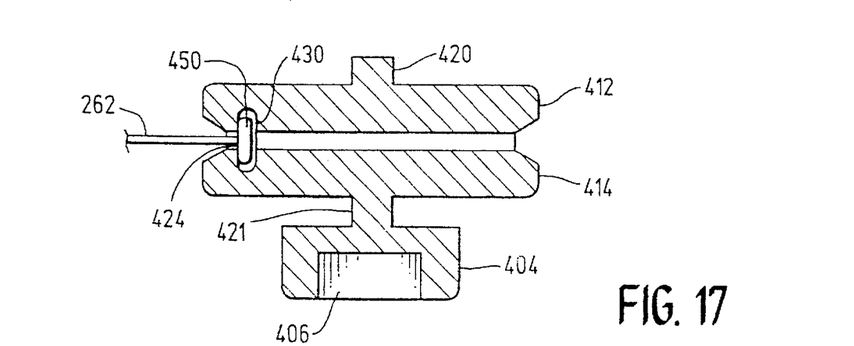
FIG. 17 is a cross-sectional view of an alternative embodiment of the central assembly of the self-locking apparatus attached to a cable having a T-shaped end.

Cable 262 has an attachment end tip 424 that has a ball 425 which fits into slot 426 formed between the wheels 412,414 as shown in FIG. 15. At the bottom of the slot 426 is a rounded recess 428 that has a diameter that is slightly larger than the diameter of the ball 425. Once the ball 425 is inserted into the slot 426 and is seated within the recess 428, it pivots within the recess 428 and is held in place as the central assembly 410 is rotated. As an alternative, in place of ball 425 the end tip 424, may have a cylindrical bar 450 at its end so that the end tip 424 is T-shaped as shown in FIG. 17. The bar 450 fits into a cylindrical recess 430 so that the bar 450 pivots within the recess 430 as the central assembly 410 is rotated. The slider block 214 has an aperture 401 through which cable 262 and end tip 424 can pass in order to removably insert the ball 425, or in the alternative the bar 450, into the slot 426 and recess 428 or 430 in the wheels 412,414.

Figure 18A:
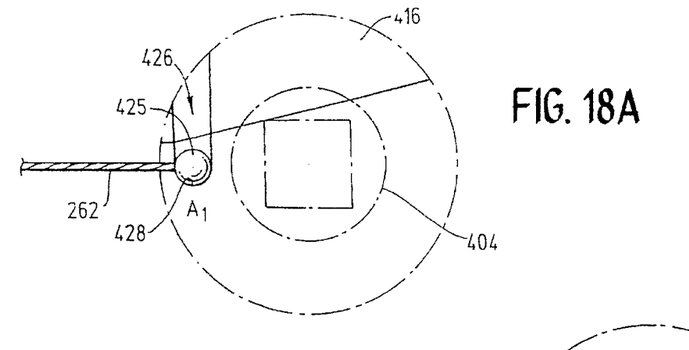
FIG. 18A is a side view of the central assembly of FIG. 16 showing the cable in the unlocked position $A_1$.
Figure 18B:
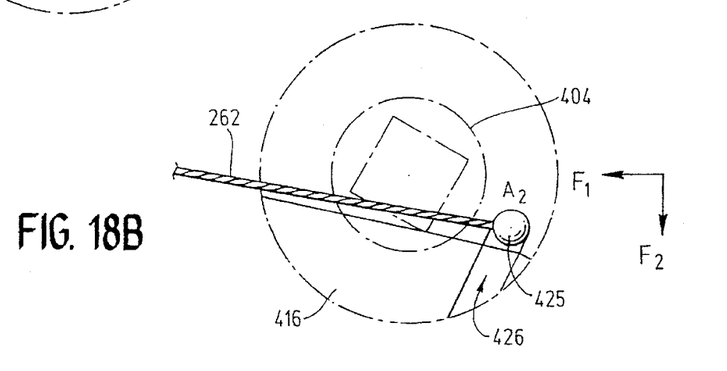
FIG. 18B is a side view of the central assembly of FIG. 16 showing the cable in the locked position $A_2$.

Referring to FIG. 18A, when the central assembly 410 is unlocked, the ball 425 of the cable 262 is at position $A_1$. As the central assembly 410 is rotated clockwise, the cable 262 moves in the direction of the rotation so that the tension on the cable 262 is increased. The cable 262 is maintained in line with the gooseneck portion 260 by the pivoting motion of the ball 425 within the recess 428 and is guided by a tapered lip portion 418 of the wheels 412,414. Once the rotation of the central assembly 410 exceeds 180 degrees from position $A_1$, the cable 262 exerts a horizontal force $F_1$ in the direction of the gooseneck portion 260 and a vertical downward force $F_2$ to pull the central assembly 410 clockwise in an attempt to return the central assembly 410 to its original position $A_1$. When the ball 425 is at position $A_2$ which is more than 180 degrees from position $A_1$, the stop 416 contacts the cable 262 and functions to block any further clockwise movement of the central assembly 410 once the cable 262 comes into contact with the stop 416. The forces $F_1$ and $F_2$ are sufficiently great to keep the cable 262 biased against the stop 416 and prevent the central assembly 410 from rotating counter clockwise so that central assembly 410 is locked at $A_2$ as shown in FIG. 18B. Thus, the locking apparatus 400 is self-locking by simply rotating the central assembly 410 a distance greater than 180 degrees from position $A_1$. The locking apparatus 400 is unlocked by rotating the central assembly 410 counter clockwise towards position $A_1$ so that the end tip 424 of the cable 262 is less than 180 degrees from position $A_1$.

When the locking apparatus 400 is in its unlocked position, $A_1$, the tension on the cable 262 is less than full tension. When the locking apparatus 400 is in its locked position, $A_2$, the cable 262 is at full tension. In this manner, the locking apparatus 400 provides a one-step tightening means for tightening the cable 262 to full tension.

As it is preferred to have the cable 262 at full tension when it is in the locked position $A_2$, the button 273 of the gooseneck portion 260 includes a cable length adjusting means 440 for varying the length of the cable according to the size of the instrument shaft being held by the gooseneck instrument holder 200. Referring to FIG. 14, in the preferred embodiment, the cable adjusting means 440 comprises the gooseneck button 273 having a threaded member 442 which threads into the exterior portion 444 of the gooseneck button 273. The exterior portion 444 is rotated about the threaded member 442 to adjust the length of the gooseneck button 273 an thus vary the distance traveled by the cable 262 between the instrument holdre tip 266 and the slider block 214. The cable length adjusting means 440 permits the user to make minor adjustments to the length of the cable 262 in order to compensate for the different shaft diameters of the various instruments capable of being held at the instrument holder tip 266 so that the cable 262 may be kept at full tension. The cable length adjusting means 440 may be any of the devices well-known in the art for adjusting the length of a cable.

To rotate the locking apparatus 400, a handle 402 may be either permanently affixed to the central assembly 410 or may be removably attached to the central assembly 410. In order to removably attach handle 402 to the central assembly 410, a socket 404 is attached to the central assembly 410 so that it protrudes from the slider block 214 as shown in FIG. 14. The socket 404 has a square head depression 406 so that a handle 402 having a square head 408 can rotate the socket 404. The square head 408 of the handle 402 is inserted into the depression 406 and the handle 402 to rotate the central assembly 410 to the locked position $A_2$ or the unlocked position $A_1$. The handle 402 may be the same square head wrench 246 discussed above used to adjust the underlying apparatus to which the gooseneck instrument holder 200 is attached.

Figure 19:
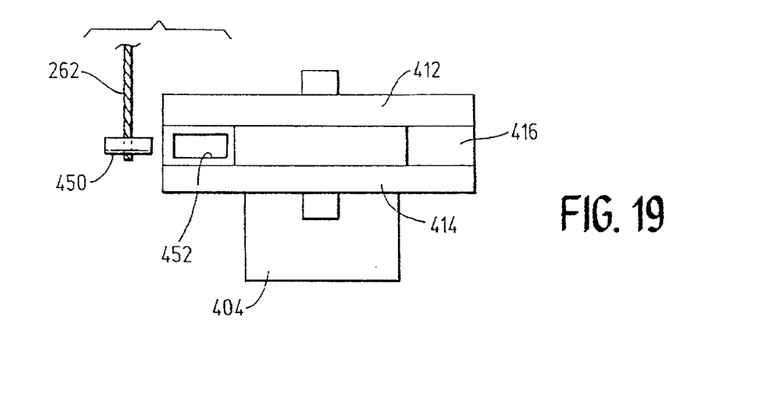
FIG. 19 is a cross-sectional view of a further alternative embodiment of the central assembly having a vertical slit into which a cable having a T-shaped end may be inserted.
Figure 20:
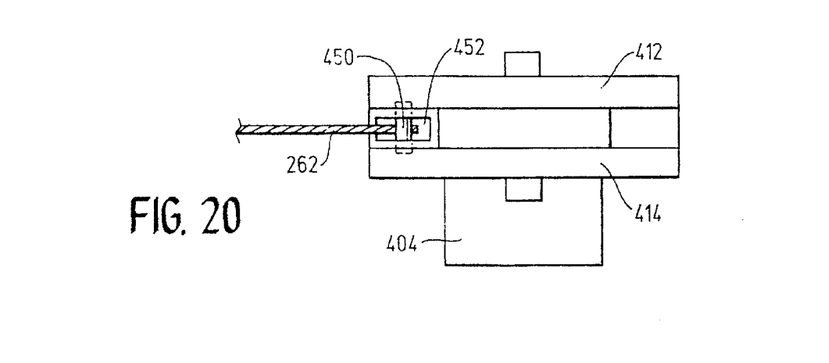
FIG. 20 is a cross-sectional view of the alternative embodiment of the central assembly in FIG. 19 with a cable having a T-shaped end inserted within the vertical slit.

As an alternative embodiment of the self-locking apparatus 400, the end tip 424 may be configured so that the cable 262 is detachably attached to the central assembly 410 and thus may be easily replaced. As shown in FIGS. 19 and 20, in place of ball 425, the end tip 424 may have a cylindrical bar 450 at its end so that the end tip 424 is T-shaped. The cylindrical bar 450 may be attached to the central assembly 410 by inserting the cylindrical bar 450 into a vertical slit 452 in the central assembly 410 as shown in FIG. 20.

The vertical slit 452 has a width that is much smaller than the length of the vertical bar 450 and a length that is slightly greater than the length of the vertical bar 450. Once the vertical bar 450 is inserted within the vertical slit 452, the vertical bar 450 is rotated 90 degrees so that it can longer pass through the vertical slit 452. To detach the vertical bar 450 from the central assembly 410, the vertical bar 450 is rotated so that is aligned lengthwise with the vertical slit 452 and passes therethrough.

Other self-locking mechanisms well known in the art such as a cam, a double linked mechanism or any other mechanism capable of moving the cable 262 from position $A_1$ to position A2, where $A_2$ is below the center line from $A_1$ may be used with the gooseneck instrument holder 200 without departing from the scope of the present invention.

Also, the gooseneck holder of the present invention is not limited to holding surgical instruments. The gooseneck holder may be adapted for use in settings where the holding and manipulation of tools is required. For example, the instrument holder tip of the present invention can be made to hold and position various tools and equipment such as, but not limited to, lights, welding instruments, lazers, drills, cameras, sensing devices, etc. so that the hands of the operator are freed while the view of the work site remains unobstructed by the gooseneck holder.

While the present invention has been disclosed and described with respect to specific embodiments, it is appreciated by those skilled in the art that various changes in form and detail may be made without departing from the spirit and scope of the invention.

What is claimed is:

1. A gooseneck instrument holder comprising a gooseneck portion terminating in means for holding an instrument, said holding means comprising means for limiting the tightening of said holding means to prevent damage to an instrument being held; and means for tightening said holding means from a position remote from said holding means.

2. The gooseneck instrument holder of claim 1 wherein said holding means includes an instrument holder tip and a portion for receiving said holder tip.

3. The gooseneck instrument holder of claims 2 wherein said end segment has a notched front end for holding said holder tip.

4. The gooseneck instrument holder of claim 3 including a central cable, said central cable engaging said holder tip whereby said central cable pulls said holder tip against said notched front end of said end segment.

5. An illuminating gooseneck instrument holder comprising: a gooseneck portion with an instrument holder tip at one end; means for tightening said gooseneck instrument holder at the other end, said tightening means comprising means for selectively tightening both said instrument holder tip and said gooseneck portion; and a fibre optic light cord having an illuminating portion positioned near the instrument holder tip end whereby said fiber optic light cord illuminates the area in which instruments being held by said instrument holder tip are used.

6. The gooseneck instrument holder of claim 5 in which said fibre optic light cord is disposed within said gooseneck instrument holder.

7. The gooseneck instrument holder of claim 5 including means for attaching said fibre optic light cord to the exterior of said gooseneck instrument holder.

8. An adjustable gooseneck apparatus comprising a flexible arm portion; a central cable terminating at one end at means for tightening said cable, said tightening means being self-locking.

9. The adjustable gooseneck apparatus of claim 8 in which said tightening means comprises an off-centered central assembly.

10. The gooseneck instrument holder of claim 9 in which said tightening means is locked by rotating said central assembly between 180 and 270 degrees.

11. The gooseneck instrument holder of claim 8 including means for stopping said tightening means.

12. The gooseneck instrument holder of claim 8 further comprising means for maintaining said cable in a selected tension.

13. The gooseneck instrument holder of claim 8 in which said central cable is at full tension when said tightening means is locked.

14. The gooseneck instrument holder of claim 8 in which said tightening means is locked or unlocked in a single step.

15. The gooseneck instrument holder of claim 8 in which said tightening means includes a handle.

16. The gooseneck instrument holder of claim 15 in which said handle is removable.

17. The gooseneck instrument holder of claim 16 in which said handle is a tool which is also useable to operate equipment associated with the use of said gooseneck instrument holder.

18. An illuminating gooseneck instrument holder, comprising:
an adjustable gooseneck portion having a central cable disposed therein; said cable terminating at one end at an instrument holder tip capable of firmly holding instruments, said cable terminating at its other end to a means for tightening the cable; an adjustable base, said adjustable base coupled to said adjustable gooseneck whereby said means for tightening said cable tightens said base, said instrument holder tip and said gooseneck; and a fibre optic light cord having an illuminating portion positioned near said instrument holder tip whereby said fibre optic cord illuminates the area in which instruments being held by the instrument holder tip are being used.

19. The gooseneck instrument holder of claim 18 including means for attaching said fibre optic light cord to said adjustable gooseneck portion.

20. The gooseneck instrument holder of claim 18 wherein said fibre optic light cord is disposed within said adjustable gooseneck portion.

* * * * *